United States Patent
Hancock et al.

(10) Patent No.: US 11,284,933 B2
(45) Date of Patent: Mar. 29, 2022

(54) ELECTROSURGICAL GENERATOR

(71) Applicant: CREO MEDICAL LIMITED, Chepstow (GB)

(72) Inventors: Christopher Paul Hancock, Bath (GB); Malcolm White, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 648 days.

(21) Appl. No.: 16/304,638

(22) PCT Filed: Jul. 11, 2017

(86) PCT No.: PCT/EP2017/067448
§ 371 (c)(1),
(2) Date: Nov. 26, 2018

(87) PCT Pub. No.: WO2018/011228
PCT Pub. Date: Jan. 18, 2018

(65) Prior Publication Data
US 2019/0209232 A1 Jul. 11, 2019

(30) Foreign Application Priority Data
Jul. 11, 2016 (GB) ..................... 1612014

(51) Int. Cl.
*A61B 18/12* (2006.01)
*A61B 18/18* (2006.01)
*A61B 18/00* (2006.01)

(52) U.S. Cl.
CPC ...... *A61B 18/1206* (2013.01); *A61B 18/1815* (2013.01); *A61B 2018/0063* (2013.01);
(Continued)

(58) Field of Classification Search
CPC ............ A61B 18/1206; A61B 18/1815; A61B 2018/00994; A61B 2018/1273;
(Continued)

(56) References Cited

U.S. PATENT DOCUMENTS

| | | | |
|---|---|---|---|
| 7,094,231 B1 * | 8/2006 | Ellman | A61B 18/1206 606/34 |
| 2003/0144680 A1 * | 7/2003 | Kellogg | A61B 17/320068 606/169 |

(Continued)

FOREIGN PATENT DOCUMENTS

| | | |
|---|---|---|
| JP | 2012-143568 A | 8/2012 |
| JP | 2014-507175 A | 3/2014 |
| WO | WO-2005115235 A1 * 12/2005 | ......... A61B 18/1815 |
| WO | WO-2017058620 A1 * 4/2017 | ......... A61B 18/1233 |

OTHER PUBLICATIONS

International Search Report and Written Opinion of related International Application No. PCT/EP2017/067448 dated Oct. 23, 2017.
(Continued)

*Primary Examiner* — Daniel W Fowler
(74) *Attorney, Agent, or Firm* — Arent Fox LLP (57) ABSTRACT

An electrosurgical generator for generating radiofrequency (RF) electromagnetic (EM) energy and microwave EM energy comprises: a microwave source for generating a microwave signal; a microwave channel for conveying the microwave signal from the microwave source to be output from the generator; an RF channel for conveying an RF signal to be output from the generator; and a microwave-to-RF converter connectable to receive the microwave signal, the microwave-to-RF converter being arranged to: generate the RF signal from the microwave signal, and deliver the RF signal to the RF channel.

16 Claims, 4 Drawing Sheets

(52) U.S. Cl.
CPC ............... *A61B 2018/00577* (2013.01); *A61B 2018/00601* (2013.01); *A61B 2018/00607* (2013.01); *A61B 2018/00922* (2013.01); *A61B 2018/00994* (2013.01); *A61B 2018/128* (2013.01); *A61B 2018/1273* (2013.01); *A61B 2018/1823* (2013.01)

(58) Field of Classification Search
CPC .. A61B 2018/00601; A61B 2018/0063; A61B 2018/00922; A61B 2018/128; A61B 2018/00607; A61B 2018/1823; A61B 18/14; A61B 2018/007232; A61B 2018/1286; A61B 2018/00958; A61B 2018/0094
See application file for complete search history.

(56) References Cited

U.S. PATENT DOCUMENTS

2017/0089962 A1* 3/2017 Moul ..................... G01R 25/00
2018/0360539 A1* 12/2018 Prakash ................. A61B 17/29

OTHER PUBLICATIONS

Search Report issued in United Kingdom Application No. GB1612014.9 dated Dec. 20, 2016.
Notice of Grounds of Rejection from the Japanese Patent Office in counterpart application No. 2018-563862, dated May 11, 2021.

* cited by examiner

ELECTROSURGICAL GENERATOR

CROSS-REFERENCE TO RELATED APPLICATIONS

This application is a National Stage entry of International Application No. PCT/EP2017/067448, filed on Jul. 11, 2017, which claims priority to United Kingdom Patent Application No. 1612014.9, filed on Jul. 11, 2016. The disclosures of the priority applications are incorporated in their entirety herein by reference.

FIELD OF THE INVENTION

The invention relates to electrosurgical apparatus in which radiofrequency energy and microwave frequency energy are used to treat biological tissue. In particular, the invention relates to surgical apparatus capable of generating radiofrequency (RF) energy for cutting tissue and microwave frequency energy for haemostasis (i.e. sealing broken blood vessels by promoting blood coagulation) or tissue ablation.

BACKGROUND TO THE INVENTION

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, it is also undesirable for a bleed to occur and not to be dealt with as soon as quickly as possible, or in an expedient manner, since the blood flow may obscure the operator's vision, which may lead to the procedure needing to be terminated and another method used instead, e.g. open surgery.

Instead of a sharp blade, it is known to use radiofrequency (RF) energy to cut biological tissue. The method of cutting using RF energy operates using the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a huge rise in the internal pressure of the cell, that cannot be controlled by the cell membrane, resulting in the cell rupturing. When this occurs over a wide area it can be seen that tissue has been transected.

Whilst the above principle works elegantly in lean tissue, it is less efficient in fatty tissue because there are fewer ionic constituents to aid the passage of electrons. This means that the energy required to vaporise the contents of the cells is much greater, as the latent heat of vaporisation of fat is much greater than that of water.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to the coagulation cascade, so clotting is enhanced. At the same time the collagen in the wall is denatured and changes from a rod like molecule to a coil, which causes the vessel to contract and reduce in size, giving the clot an anchor point, and a smaller area to plug.

However, RF coagulation is less efficient when fatty tissue is present because the electrical effect is diminished. It can thus be very difficult to seal fatty bleeders. Instead of having clean white margins, the tissue has a blackened, burned appearance.

In practice, a RF device may operate using a waveform with a medium crest factor that is midway between a cutting and coagulating output.

GB 2 486 343 discloses a control system for an electrosurgical apparatus in which the energy delivery profile of both RF energy and microwave energy delivered to a probe is set based on sampled voltage and current information of RF energy conveyed to the probe and sampled forward and reflected power information for the microwave energy conveyed to and from the probe.

Figure 1:
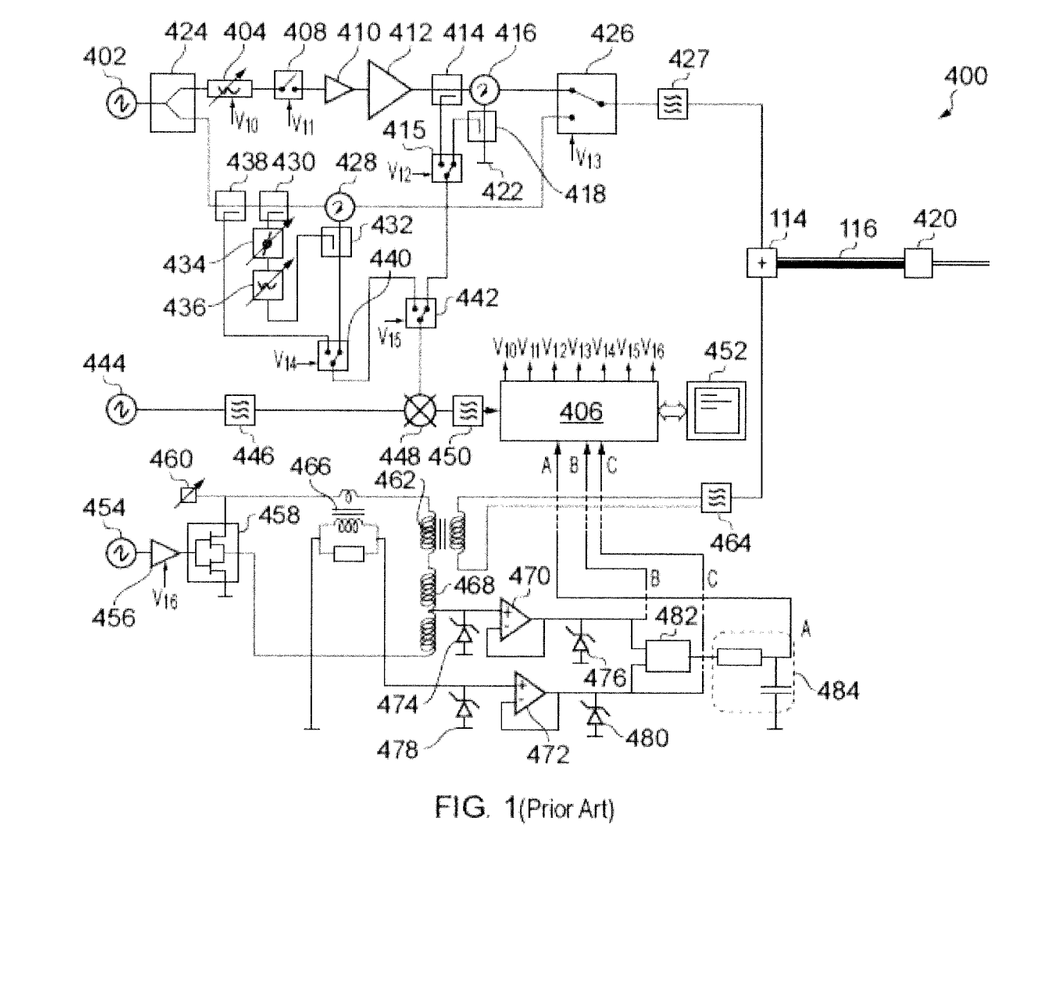
FIG. 1 is a schematic system diagram of a known electrosurgical generator configuration for providing microwave and RF signals, and is described above.

FIG. 1 shows a schematic diagram of an electrosurgical apparatus 400 as set out in GB 2 486 343. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal V10 and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection The other branch from the power splitter 424 forms a measurement channel. The measurement channel bypasses the amplifying line-up on the microwave channel, and hence is arranged to deliver a low power signal from the probe. In this embodiment, a primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit is used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel.

The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452, as discussed above.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 114, which conveys both types of signal separately or simultaneously along cable assembly 116 to the probe 420, from which it is delivered (e.g. radiated) into the biological tissue of a patient. A suitable signal combiner is disclosed in WO 2014/049332.

SUMMARY OF THE INVENTION

At its most general, the present invention proposes an electrosurgical generator in which both microwave and RF signals are derived from a signal frequency source. Such a generator may be capable of delivering RF energy in waveforms suitable for cutting (e.g. resection or dissection) or coagulation as well as delivering microwave energy suitable for coagulation, ablation or measurement. The invention may enable a reduction in the number of components required in a multi-frequency electrosurgical system. This can reduce manufacturing costs and may also facilitate the fabrication of smaller scale devices, e.g. portable or handheld electrosurgical generators.

According to the invention, there is provided an electrosurgical generator for generating radiofrequency (RF) electromagnetic (EM) energy and microwave EM energy, the generator comprising: a microwave source for generating a microwave signal; a microwave channel for conveying the microwave signal from the microwave source to be output from the generator; an RF channel for conveying an RF signal to be output from the generator; a microwave-to-RF converter connectable to receive the microwave signal, the microwave-to-RF converter being arranged to: generate the RF signal from the microwave signal, and deliver the RF signal to the RF channel. In this arrangement the same energy source (the microwave source) is used to create the RF signal and the microwave signal. This means that only a single power source is needed in the generator line up, which can reduce the number of components compared with known systems.

The microwave source may comprise a power amplifier, e.g. capable of outputting microwave energy at a power of 100 W or more at a single stable microwave frequency.

The microwave-to-RF converter may include: a RF switching unit arranged to introduce an RF characteristic into the microwave signal; and a rectifying unit for rectifying the microwave signal while preserving the RF characteristic, wherein the RF signal is obtained from an output of the rectifying unit. The RF characteristic may be introduced in a manner that ensure that no or a negligible amount of power is lost in the microwave signal. For example, the RF switching unit may be a modulator capable or rapid switching, e.g. implemented using fast switching PIN diodes or the like, or a SPDT switch that alternates the microwave signal between different destinations.

The rectifying unit is arranged to convert the microwave (i.e. GHz-order frequency) signal into a DC signal. By introducing the RF characteristic as a substantially instantaneous ON-OFF transition within the microwave signal, the rectification of the microwave signal may have little or no impact on the RF characteristic. Preserving the RF characteristic at this stage enables it to be used to extract a desired waveform for the RF signal. In the examples given herein, the output RF signal may have a sinusoidal form, i.e. may be substantially a single stable frequency.

The rectifying unit may operate as full-wave rectifier for the microwave signal, so that all of the microwave waveform can be utilised.

The RF characteristic may comprise a principle RF component having a single frequency between 100 kHz and 300 MHz, preferably 400 kHz. The RF switching unit may operate at the principle RF component frequency.

In one example, the RF switching unit may comprise a modulator for pulsing the microwave signal at a frequency less than 300 MHz. The modulator may be arranged to operate at a duty cycle of 50%. This set up can maximise the amplitude of the fundamental frequency (which may correspond to the principle RF component) in the resulting square wave.

In another example, the rectifying unit may comprise a first rectifier and a second rectifier, and the RF switching unit may be arranged to alternate the microwave signal between the first rectifier and the second rectifier at a frequency less than 300 MHz. The microwave-to-RF converter may be arranged to form a composite rectified signal from rectified signals output from the first rectifier and the second rectifier. In one example, the polarities of the first rectifier and the second rectifier may be opposite so that the composite signal is a square wave having an amplitude double that of the first rectifier or second rectifier alone.

The microwave-to-RF converter may comprise a filtering unit arranged to remove unwanted frequency components from the output of the rectifying unit. In other words, the filtering unit may be arranged to select a desired frequency or narrow band of frequencies from the output of the rectifier unit. Where the output is a square wave, the filtering unit may be arranged to remove the higher harmonics from the signal. The RF signal may thus be based primarily on the fundamental of the square wave.

In order to achieve a desired voltage level for the RF signal, the microwave-to-RF converter may comprise a step-up transformer.

The generator may be configured to deliver the microwave energy and the RF signal separately, e.g. in a mutually exclusive manner. The generator may thus comprise a switch for selectively directing the microwave signal to the microwave channel or the microwave-to-RF converter.

The generator may comprise a common output channel for conveying the microwave signal and RF signal towards the delivery probe. A signal combiner may be provided connecting the microwave channel and the RF channel to the common output channel. The signal combiner may be a switch or a diplexer.

Operation of the generator may be managed by a controller, e.g. a microprocessor or the like. The controller may be arranged to operate the microwave-to-RF converter, e.g. by sending appropriate control signals to the RF switching unit and/or rectifying unit.

In another aspect, the invention provides an electrosurgical system for delivering radiofrequency (RF) electromagnetic (EM) energy and microwave EM energy into biological tissue, the system comprising: an electrosurgical generator as defined above; and a delivery probe connected to receive the microwave signal and RF signal from the electrosurgical generator. The delivery probe may be an electrosurgical instrument capable of delivering RF energy to cut biological tissue, and microwave energy to coagulate or ablate biological tissue.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz.

BRIEF DESCRIPTION OF THE DRAWINGS

Examples of the present invention are discussed in detail below with reference to the accompanying drawings, in which.

DETAILED DESCRIPTION; FURTHER OPTIONS AND PREFERENCES

Figure 2:
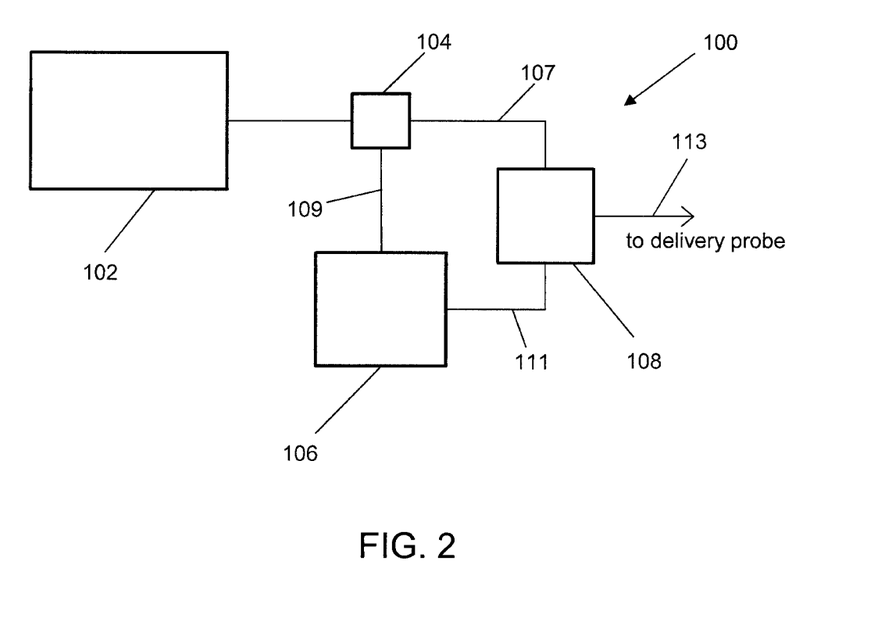
FIG. 2 is a schematic block diagram of an electrosurgical generator having a microwave-to-RF converter that is an embodiment of the invention.

FIG. 2 is a schematic block diagram of an electrosurgical apparatus 100 for generating microwave energy and RF energy for treating biological tissue that is an embodiment of the invention. The apparatus 100 comprises a microwave generator 102 for generating a microwave signal having a single stable frequency. A preferred frequency is 5.8 GHz. The microwave generator 102 may comprise the components on the microwave channel discussed above with reference to FIG. 1. In particular, the microwave generator 102 may comprise a power amplifier capable of launching the microwave signal at a power of 100 W into a load having an 50Ω impedance.

The microwave signal output from the microwave generator 102 is received by a mode switch 104 which is controlled by a controller (not shown) to select a path for the microwave signal. The controller can operate the mode switch 104 to select between a microwave delivery mode, in which the microwave signal is directed along a first path 107 towards a delivery probe (not shown), and an RF delivery mode, in which the microwave signal is directed along a second path 109 towards a microwave-to-RF converter 106 that converts the microwave signal to an RF signal which is conveying along a third path 111 towards the delivery probe. The microwave-to-RF converter 106 is discussed in more detail below.

The first path 107 and second path 109 may be formed from transmission lines (e.g. coaxial cables or similar) that can convey high power microwave energy at low loss. Similarly, the mode switch 104 may be a coaxial switch (e.g. a coaxial single pole, double throw switch) or the like. The third path 111 may be formed from a transmission line that is suitable for conveying an RF signal with low loss. Again, a coaxial cable may be suitable.

A signal combiner 108 may be used to convey the RF signal from the third path 111 or the microwave signal from the second path 109 on a common output path 113 toward the delivery probe. The signal combiner 108 may be a switch or a diplexer arrangement that protects the microwave-to-RF converter 106 and microwave generator 102 from energy that is reflected back from the probe. If a switch is used in the signal combiner 108, it may be operable by the controller in synchronisation with the mode switch 104.

The delivery probe may be any electrosurgical instrument suitable for using RF energy and microwave energy on biological tissue, e.g. for cutting, coagulation, measurement, ablation or the like. Possible probes can be found in WO 2014/006369, WO 2014/184544 and WO 2015/097446, for example. The delivery probe may be used in any of open surgery, laparoscopic procedures and endoscopic procedures. In some example, the signal combiner 108 may be arranged to transfer the RF signal and microwave signal to a flexible feed cable (e.g. a coaxial cable) that passes through the instrument channel of a surgical scoping device.

Figure 3:
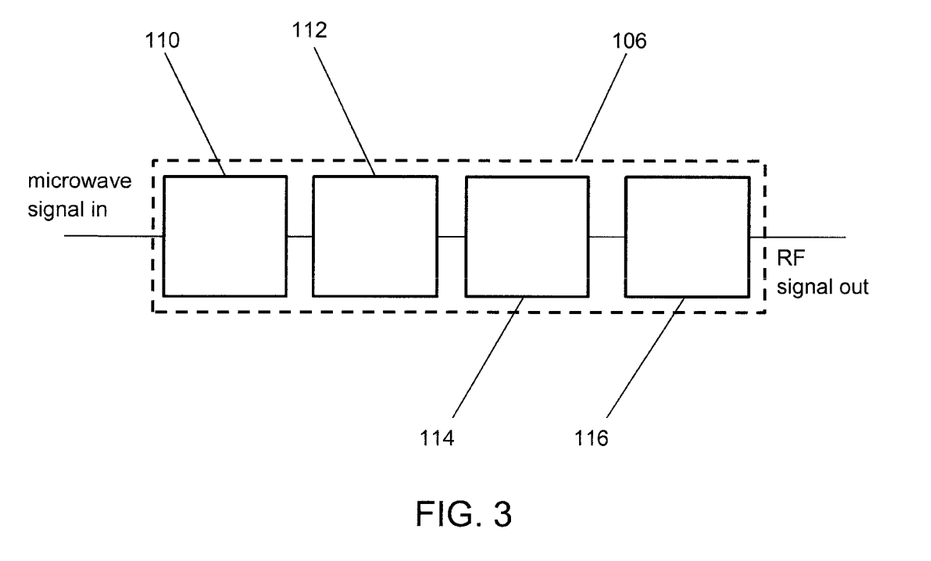
FIG. 3 is a schematic block diagram of the components in a microwave-to-RF converter that can be used in an embodiment of the invention.

FIG. 3 is a schematic block diagram of the functional elements of the microwave-to-RF converter 106 used in embodiments of the invention. It can be understood that the a variety of combinations of components can be selected to perform the functions of the blocks in FIG. 3, and the invention need not be limited to any particular combination of components.

The microwave-to-RF converter 106 comprises an RF switching unit 110, which may be a modulator for pulsing the microwave signal or a switch for directing the microwave signal between a plurality of paths. These two alternatives are discussed in more detail below with reference to FIGS. 4 and 5. The RF switching unit 110 operates to introduce an RF characteristic to the microwave signal. The RF characteristic includes a frequency component that corresponds to the desired principle frequency of the RF signal that is to be output from the converter 106. For example, the microwave signal may be input to the converter 106 as a continuous wave (CW) signal. The RF switching unit 110 may be arranged to transform the CW microwave signal into one or more pulsed microwave signal, where the pulse frequency possesses the RF characteristic. The RF switching unit 110 may operate under the control of the controller (not shown). The RF switching unit 110 may be formed using PIN diodes, which are capable of fast switching at high power signals.

The output of the RF switching unit 110 is received by a rectifying unit 112, which is arranged to rectify the microwave signal, i.e. convert the microwave frequency AC component of each pulse of the pulsed microwave signal into a DC signal. Any suitable rectifier circuitry may be used for this purpose, although, as discussed below, it is desirable for the conversion efficiency to be high. The rectifier may comprise a reverse amplifier arrangement, e.g. using a Schottky diode or the like. The rectifier is preferably a full-wave rectifier, e.g. having a full bridge configuration. This arrangement makes full use of the microwave signal, which can assist in obtaining an RF signal having a desired voltage. The rectifying unit 112 may include a smoothing capacitor arrangement, e.g. provided by a varactor diode or the like connected in shunt to the rectifier output.

The output of the rectifying unit 112 is received by a filtering unit 114 that is arranged to extract a desired RF signal from the rectified signal. The rectified signal may resemble a square wave, i.e. a sequence of ON and OFF pulses at an RF frequency introduced by the RF switching unit 110. The filtering unit 114 may be arranged to remove the higher harmonic content of the rectified signal to produce an output RF signal whose dominant constituent is a sinusoidal wave at the fundamental frequency.

The output of the filtering unit is received by a transformer unit 116 whose function is to step up the voltage of the RF signal to a level desired for use. Any conventional step-up transformer configuration can be used for this purpose. In one example, the step-up transformer may be incorporated into the transformer 462 discussed above with reference to FIG. 1. In other words, the converter 106 may be implemented in a system similar to that shown in FIG. 1, where it replaces the components that generate the RF signal.

The configuration of the microwave-to-RF converter 106 and the output power of the microwave generator 102 when switched to generate RF energy may be selected to enable an RF signal having properties suitable for treating biological tissue to be produced. For example, it may be desirable for the generated RF signal to be used in a process for cutting biological tissue.

In one example, the desired output voltage of the RF signal is about 300 V rms. The RF signal is likely to "see" a relatively high impedance, e.g. of about 1 kΩ or more. In this situation, the RF signal would result in 300 mA rms current, which therefore corresponds to about 90 W of RF power. The power of the input microwave signal and the efficiency of the microwave-to-RF converter 106 are therefore preferably selected to enable this level of power to be generated. For example, if the microwave signal has a power of 100 W in 50Ω, the conversion efficiency would need to be 90%.

If 90% efficiency cannot be achieved it may be necessary to operate into a higher impedance than 1 kΩ (i.e. with a lower current than 300 mA rms), or with a lower RF voltage than 300 V rms.

For the purposes of a simple illustration of the operation of the microwave-to-RF converter 106, the following analysis is based on what could be achieved with a 100% efficiency.

If a CW microwave signal having 100 W in 50Ω is rectified with 100% efficiency using a full wave rectifier, the rectified voltage is 100 V. The RF signal can be produced by switching the microwave power on and off at the RF frequency (400 kHz cycle frequency). This will produce a 400 kHz signal alternating between 100 V and 0 V, i.e. 100 V peak-to-peak. This is a square wave, which has a high harmonic content ($3^{rd}$, $5^{th}$, $7^{th}$, etc.). If this is filtered to select only the fundamental (at 400 kHz) the amplitude of the fundamental sinusoidal wave will be 127.4% of the amplitude of the square wave, i.e. 127.4 V peak-to-peak. The square wave, i.e. 50% duty cycle, maximises the amplitude of the fundamental compared to other duty cycles. This method of operation is discussed below with respect to FIG. 4.

However, the peak-to-peak voltage can be doubled if the rectifier output is reversed rather than switched off, to generate ±100 V. This would give a peak-to-peak voltage of 200 V before filtering, and about 254.8 V peak-to-peak at 400 kHz. To do this the rectifier polarity can be switched at 400 kHz cycle frequency. One way of doing this is to use a pair of microwave switches and two opposite polarity full-wave rectifiers. This method of operation is discussed below with respect to FIG. 5.

The peak-to-peak voltage for a 300 V rms signal is 848.5 V peak-to-peak. The step-up transformer can therefore be arranged as a 3:10 voltage transformer to transform the 254 V peak-to-peak to the desired level. A 3:10 voltage transformer will transform the impedance by 9:100, i.e. from 50Ω to 555.5Ω, so the apparatus may be configured to ensure that the output impedance is at a level that supports the rectifying unit to deliver the peak output as calculated above.

Figure 4:
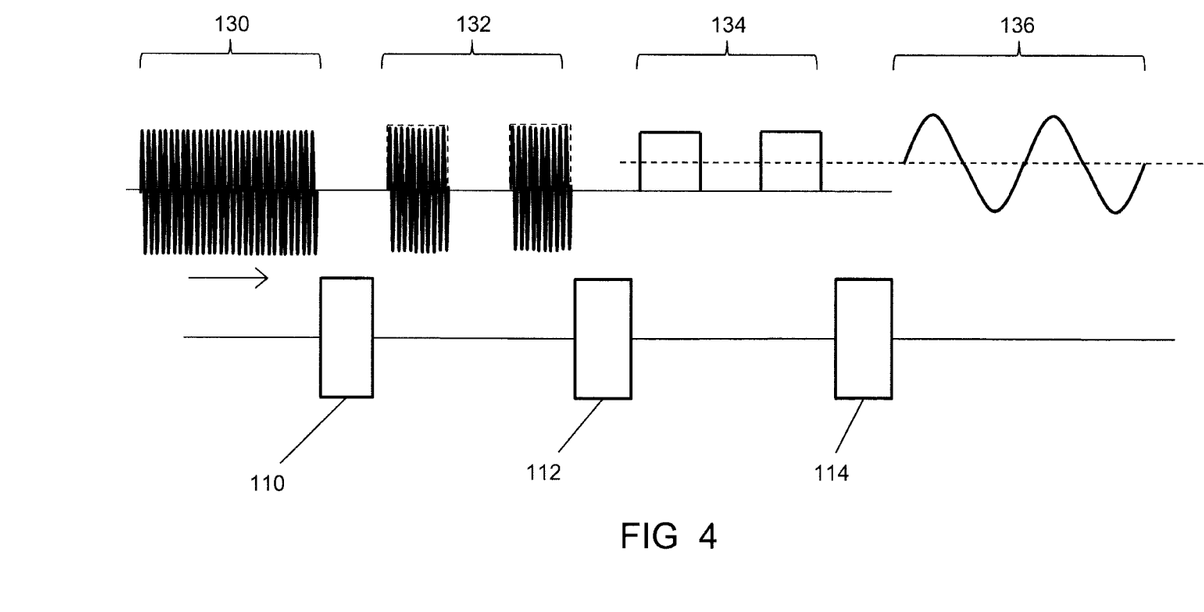
FIG. 4 is a schematic diagram showing the stages of signal transition in a first example of a microwave-to-RF converter that can be used in the invention.

FIG. 4 is a schematic illustration of how the microwave signal is transformed by a microwave-to-RF converter in one embodiment.

The microwave signal is input to the converter as a CW microwave signal 130, which is received by an RF switching unit 110, which in this example is a modulator, e.g. a PIN diode-based device operated by a controller (not shown). The output of the RF switching unit 110 is a pulsed microwave signal 132 that comprises a plurality of microwave energy bursts.

The pulsed microwave signal 132 is received by a full-wave rectifier unit 112 that rectifies each burst of microwave energy to form a rectified signal 134 that resembles a square wave formed by a sequence of ON and OFF portions. The duty cycle of the square wave corresponding to the switching duty cycle of the RF switching unit. In this example the duty cycle is 50%. The frequency of the microwave signal may be 5.8 GHz, whereas the switching frequency of the RF switching unit may be 400 kHz. The waveforms depicted in FIG. 4 are not to scale, but are generally indicative of the fact that the frequency of the square wave is many orders of magnitude (e.g. at least three orders of magnitude) less than the frequency of the microwave signal.

The rectified signal 134 is received by a filtering unit 114, which filters out the higher harmonics in the square wave signal and outputs an RF signal 136 having a frequency that corresponds to the fundamental frequency of the square wave. The RF signal 136 can then be conveyed to a step-up transformer as discussed above for delivery to the probe.

Figure 5:
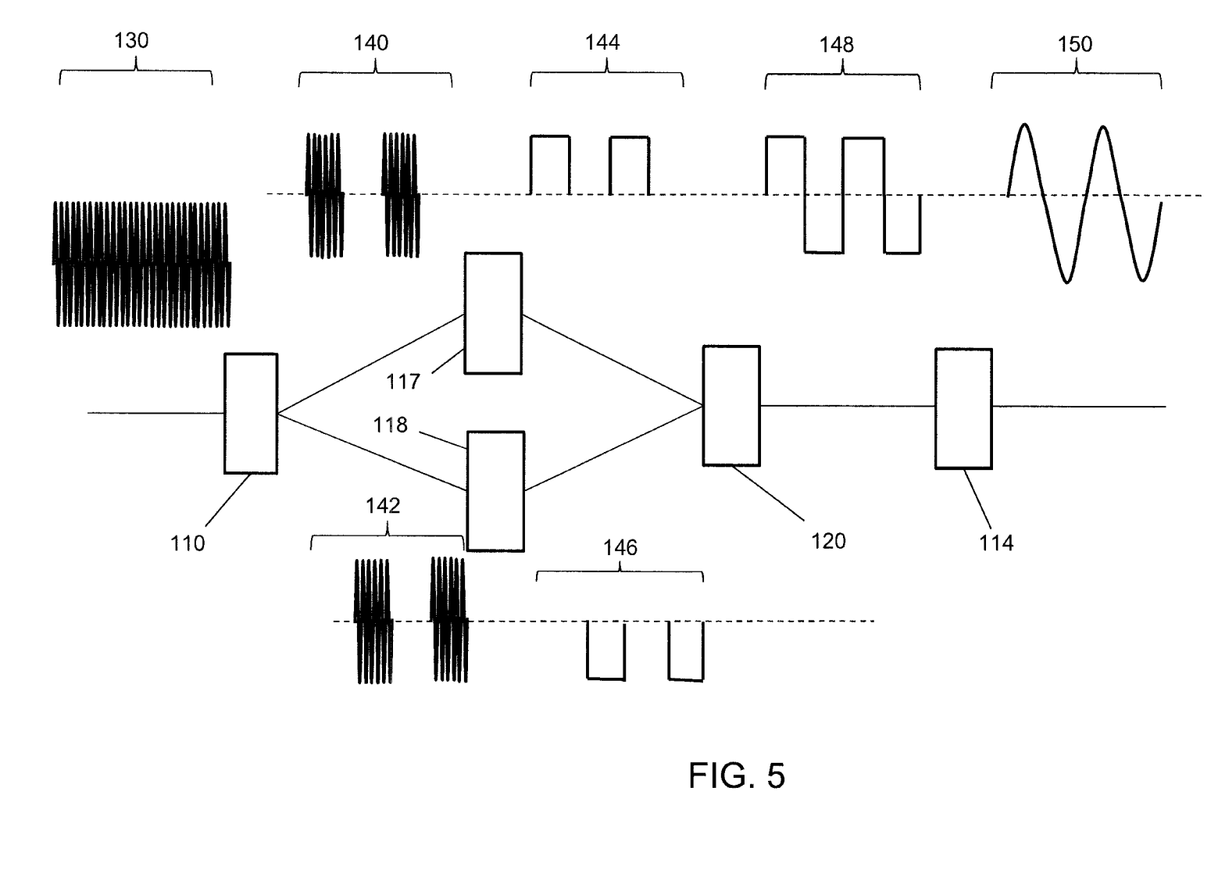
FIG. 5 is a schematic diagram showing the stages of signal transition in a second example of a microwave-to-RF converter that can be used in the invention.

FIG. 5 is a schematic illustration of how the microwave signal is transformed by a microwave-to-RF converter in another embodiment.

In this example, the microwave signal is also input to the converter as a CW microwave signal 130. The CW microwave signal 130 is received by an RF switching unit 110, which in this example is a switch, e.g. a high power switch manufactured by Teledyne Technologies Incorporated. The RF switching unit 110 alternates the CW microwave signal 130 between two rectifier units 117, 118. A first rectifier unit 117 therefore receives a first pulsed microwave signal 140 that comprises a plurality of microwave energy bursts, while a second rectifier unit 118 receives a second pulsed microwave signal 142 that is out of phase with the first pulsed microwave signal 140 such that the bursts of microwave energy are received alternately in the first rectifier unit 117 and the second rectifier unit 118.

Each rectifier unit 117, 118 rectifies the bursts of microwave energy to form a respective rectified signal 144, 146 that resembles a square wave formed by a sequence of ON and OFF portions. The duty cycle of the square wave corresponding to the switching duty cycle of the RF switching unit 110. In this example the duty cycle is 50%, so the resulting rectified signals 144, 146 have the same frequency. The frequency of the microwave signal may be 5.8 GHz, whereas the switching frequency of the RF switching unit may be 400 kHz. The waveforms depicted in FIG. 5 are not to scale, but are generally indicative of the fact that the frequency of the square wave is many orders of magnitude (e.g. at least three orders of magnitude) less than the frequency of the microwave signal.

The polarity of the second rectifier unit 118 is arranged to be opposite to that of the first rectifier unit 117. The output from the rectifier units 117, 118 thus comprises a first rectified signal 144 and a second rectified signal 146 with opposite polarities and a phase offset.

The first rectified signal 144 and the second rectified signal 146 are combined into a composite signal 148 by a switching unit 120, whose switching frequency is the same as switching unit 110 and whose operation may be synchronised with the switching unit 110 by the controller (not shown). The composite signal 148 is a square wave having twice the amplitude of each rectified signal 144, 146.

The composite signal 148 is received by a filtering unit 114, which filters out the higher harmonics in the square wave signal and outputs an RF signal 150 having a frequency that corresponds to the fundamental frequency of the square wave. The RF signal 150 can then be conveyed to a step-up transformer as discussed above for delivery to the probe.

The invention claimed is:

1. An electrosurgical generator for generating radiofrequency (RF) electromagnetic (EM) energy and microwave EM energy, the generator comprising:
   a microwave source for generating a microwave signal;
   a microwave channel for conveying the microwave signal from the microwave source to be output from the generator;
   an RF channel for conveying an RF signal to be output from the generator for treating biological tissue;
   a microwave-to-RF converter connectable to receive the microwave signal, the microwave-to-RF converter being arranged to:
   generate the RF signal from the microwave signal, and deliver the RF signal to the RF channel.

2. An electrosurgical generator according to claim 1, wherein the microwave-to-RF converter includes:
   a RF switching unit arranged to introduce an RF characteristic into the microwave signal; and
   a rectifying unit for rectifying the microwave signal while preserving the RF characteristic,
   wherein the RF signal is obtained from an output of the rectifying unit.

3. An electrosurgical generator according to claim 2, wherein the rectifying unit operates as full-wave rectifier for the microwave signal.

4. An electrosurgical generator according to claim 2, wherein the RF characteristic comprises a principle RF component having a frequency of 400 kHz.

5. An electrosurgical generator according to claim 2, wherein the RF switching unit comprises a modulator for pulsing the microwave signal at a frequency less than 300 MHz.

6. An electrosurgical generator according to claim 5, wherein the modulator is arranged to operate at a duty cycle of 50%.

7. An electrosurgical generator according to claim 6, wherein the rectifying unit is arranged to output a square wave.

8. An electrosurgical generator according to claim 2, wherein the rectifying unit comprises a first rectifier and a second rectifier, and wherein the RF switching unit is arranged to alternate the microwave signal between the first rectifier and the second rectifier at a frequency less than 300 MHz.

9. An electrosurgical generator according to claim 8, wherein the microwave-to-RF converter is arranged to form a composite rectified signal from rectified signals output from the first rectifier and the second rectifier.

10. An electrosurgical generator according to claim 9, wherein the composite rectified signal is a square wave.

11. An electrosurgical generator according to claim 2, wherein the microwave-to-RF converter comprises a filtering unit arranged to remove unwanted frequency components from the output of the rectifying unit.

12. An electrosurgical generator according to claim 2, wherein the microwave-to-RF converter comprises a step-up transformer.

13. An electrosurgical generator according to claim 1 including a switch for selectively directing the microwave signal to the microwave channel or the microwave-to-RF converter.

14. An electrosurgical generator according to claim 1 including a signal combiner for connecting the microwave channel and the RF channel to a common output channel.

15. An electrosurgical generator according to claim 1 including a controller arranged to operate the microwave-to-RF converter.

16. An electrosurgical system for delivering radiofrequency (RF) electromagnetic (EM) energy and microwave EM energy into biological tissue, the system comprising:
    an electrosurgical generator according to claim 1;
    a delivery probe connected to receive the microwave signal and RF signal from the electrosurgical generator.

* * * * *